United States Patent [19]

Yamada et al.

[11] Patent Number: 5,711,881
[45] Date of Patent: Jan. 27, 1998

[54] HEMATOPOIETIC INHIBITING FACTOR CONTAINING COMPOSITIONS

[75] Inventors: Satoko Yamada, Kusatsu; Hiroshi Kataoka, Otsu, both of Japan

[73] Assignee: Toray Industries, Inc., Tokyo, Japan

[21] Appl. No.: 284,477

[22] PCT Filed: Dec. 3, 1993

[86] PCT No.: PCT/JP93/01766

§ 371 Date: Oct. 6, 1994

§ 102(e) Date: Oct. 6, 1994

[87] PCT Pub. No.: WO94/13702

PCT Pub. Date: Jun. 23, 1994

[30] Foreign Application Priority Data

Apr. 12, 1992 [JP] Japan .................. 4-325453

[51] Int. Cl.$^6$ .................. A61M 1/16; B01D 13/00
[52] U.S. Cl. .................. 210/500.21; 210/646; 210/500.22; 210/500.23; 210/500.27; 210/500.3; 210/500.35; 210/500.41; 210/500.43; 424/529; 530/380
[58] Field of Search .................. 424/529; 530/380; 210/500.35, 646, 500.21, 500.22, 500.23, 500.27, 500.3, 500.41, 500.43

[56] References Cited

U.S. PATENT DOCUMENTS 4,925,534   5/1990   Kataoka et al. .................. 210/500.35

*Primary Examiner*—Herbert J. Lilling
*Attorney, Agent, or Firm*—Morrison & Foerster LLP

[57] ABSTRACT

The present invention relates to hematopoietic inhibiting factor-containing compositions which inhibit colony formation of CFU-E, comprising a substance obtained in the fraction eluting at exclusion limit by gel filtration using a gel having maximum molecular weight fractionation of not less than 200,000 and not more than 1,500,000, of a dialysate of blood which is obtained with a dialysis membrane having albumin sieving coefficient of not less than 0.01, followed by concentration with a membrane having molecular weight fractionation of not more than 5,000, and hematopoietic inhibiting factor-containing compositions which inhibit colony formation of CFU-E can be obtained. It further relates to a process of treating blood in which AI component is so removed as to satisfy AI/AA≧1/50, wherein AI is the height of the absorbancy value of the hematopoietic inhibiting factor-containing compositions and AA is the height of the maximum absorbancy value in a gel filtration pattern of solutes of the dialysate expressed in terms of the absorbancy at 280 nm, and to a dialysis membrane which satisfies AI/AA≧1/50. It further relates to drug compositions and a therapeutic agent for erythrocytosis, containing such hematopoietic inhibiting factor as the active ingredient.

5 Claims, 1 Drawing Sheet the gel filtration pattern with Sephacryl S-200HR

HEMATOPOIETIC INHIBITING FACTOR CONTAINING COMPOSITIONS

DESCRIPTION

TECHNICAL FIELD

The present invention relates to hematopoietic inhibiting factor-containing compositions which inhibit colony formation of colony forming unit-erythroidan erythroid colony forming cell (hereinafter referred to as CFU-E).

BACKGROUND ART

It is reported that the volume of packed red cells (hematocrit) in the majority of patients under therapeutic hemodialysis is 20–30%, which shows an extreme anemic condition compared to the hematocrit of 40–50% in a healthy subject. Meanwhile, erythropoietin, a hemopoietic stimulator has been developed and its massive administration, with the dosage amounting to 30 times the concentration in blood of a healthy subject, has been known to improve the anemia. What has been made clear recently is that though the massive administration of the erythropoietin improves anemia in many patients, some of the patients are left unimproved.

Considering that the massive administration of the hemopoietic stimulating erythropoietin is required, and that there are still some patients whose anemic conditions are left unimproved even by such massive administration of erythropoietin, it can be deemed that a hematopoietic inhibiting substance might be stored in a hemodialysis patient to interfere the activity of the erythropoietin.

Regarding the hematopoietic inhibiting substance, there is a report of Saito et al. (Clinical Chemistry, A. Saito et al. (1986) P1938), for example, wherein they have reported that a hematopoietic inhibiting factor had a molecular weight of 1,000–10,000. If the hematopoietic inhibiting factor had such a molecular weight, the anemia of the hemodialysis patients should have been sufficiently improved by the dialysis utilizing a dialysis membrane used in the present therapeutic hemodialysis which could remove a medium molecular weight substance, however, actually their anemia has not been fully improved yet.

The invention of this application is aimed at solving the above-described problems of the known art, accordingly, its object is to provide accurate hematopoietic inhibiting factor-containing compositions which inhibit colony formation of CFU-E.

DISCLOSURE OF THE INVENTION

The invention of this application relates to hematopoietic inhibiting factor-containing compositions, which are obtained by separating a component having a molecular weight of 200,000 or more from a dialysate obtained by dialyzing blood with a dialysis membrane of a sieving coefficient of not less than 0.01. More specifically, it relates to hematopoietic inhibiting factor-containing compositions which inhibit colony formation of CFU-E, comprising compositions obtained in a fraction eluting at exclusion limit (first fraction) by gel filtration using a gel having maximum molecular weight fractionation of not less than 200,000 and not more than 1,500,000, of a dialysate of blood which is obtained with a dialysis membrane having albumin sieving coefficient of not less than 0.01, followed by concentration with a membrane having molecular weight fractionation of not more than 5,000.

It further relates to a process of treating blood in which AI component is so removed as to satisfy AI/AA≧1/50, wherein AI is the height of the absorbancy value of the hematopoietic inhibiting factor-containing compositions according to claims 1–5 and AA is the height of the maximum absorbancy value in a gel filtration pattern of solutes of the dialysate expressed in terms of the absorbancy at 280 nm, and to a dialysis membrane which satisfies AI/AA≧1/50, wherein AI is the height of the absorbancy value of the hematopoietic inhibiting factor-containing compositions according to claims 1–5 and AA is the height of the maximum absorbancy value in a gel filtration pattern of solutes of the dialysate expressed in terms of the absorbancy at 280 nm. It further relates to drug compositions and a therapeutic agent for erythrocytosis, containing such hematopoietic inhibiting factor as the active ingredient.

THE BEST MODE FOR CARRYING OUT THE INVENTION

Figure 1:
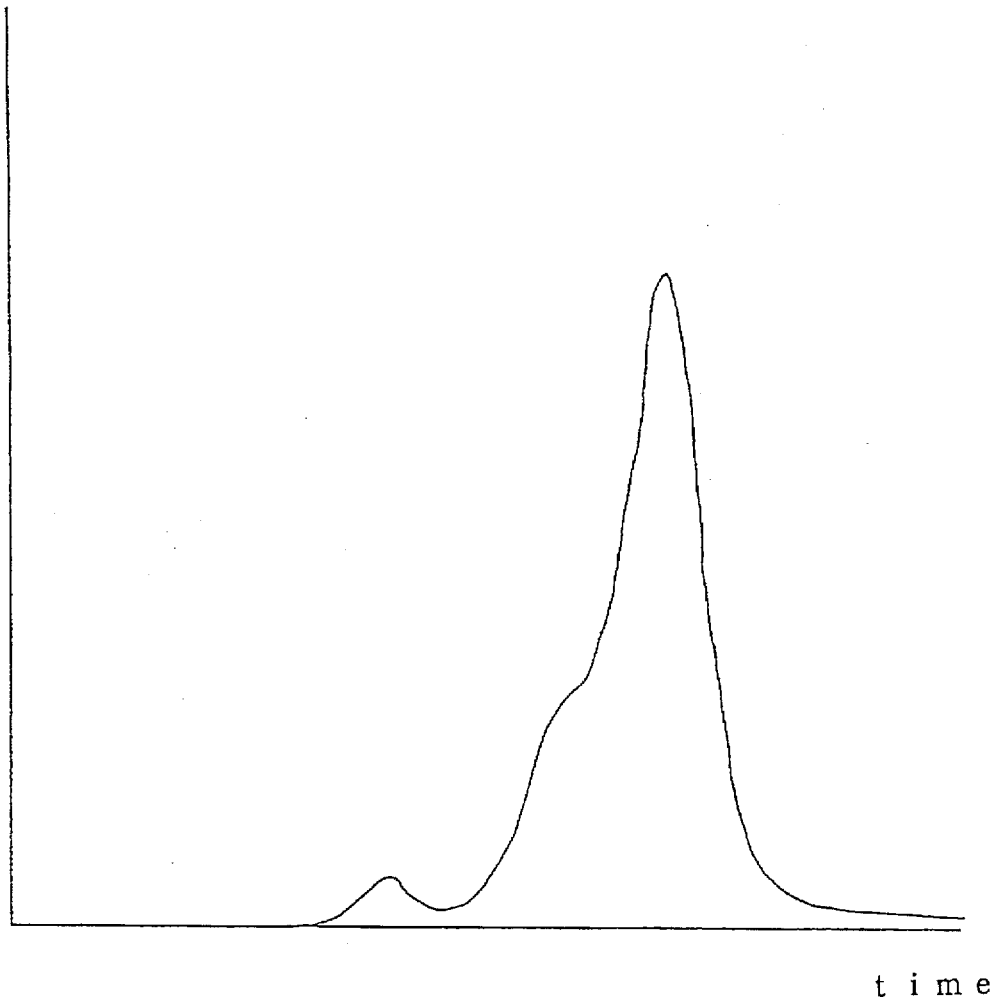
FIG. 1 is a chart showing a gel filtration pattern according to the Embodiment 2 of the invention of this application.

According to the present invention, a dialysis membrane of any material can be used without any restriction as far as it has albumin sieving coefficient of not less than 0.01, for example, a membrane described in Japanese Patent Laid-Open Sho 63–109871 can be used as such a dialysis membrane.

Particularly preferable is a membrane obtained in the following process. A high polymer is dissolved in its solvent, and spun into an aqueous solidifying bath through a ring spinning nozzle to produce a permeable hollow fiber, wherein the texture of the membrane is formed by controlling the concentration of the polymer solution, the cooling conditions and the solvent removing speed during solidifying and hardening process. For example, when polymethyl methacrylate polymer is used as a membrane material for producing a hollow fiber membrane, isotactic polymethyl methacrylate and syndiotactic polymethyl methacrylate produced by suspension polymerization are dissolved in a solvent such as dimethyl sulfoxide to make a polymer concentration of 15–27% by weight. The resulting solution is delivered through the ring spinning nozzle, while dry nitrogen gas is introduced from inside and a cooling gas is blown from outside to form the hollow fiber. At that time, the cooling gas preferably has a dry-bulb temperature of 5°–17° C., and a dew point of −5°–5° C., which is an index showing the water content. Then it is led to a solidifying bath mainly containing water, solidified and the solvent is removed. The solidifying bath preferably has a temperature of 20°–40° C.

As a membrane to be used for condensation which has molecular weight fractionation of not more than 5,000, any generally-used membrane having the molecular weight fractionation of not more than 5,000 can be used without any restriction, illustratively such membrane includes cellulose membrane, cellulose acetate membrane, polyacrylonitrile membrane and polysulfone membrane. According to the present invention, the condensation ratio is not specifically limited, however, it is preferable to carry out condensation to a high concentration of 200 times or higher, from the view point of carrying out fractionation, dispensing, and biological activity evaluation. In order to analyse AI/AA, 100-fold concentration can be acceptable.

The gel of the present invention which has maximum molecular weight fractionation of not less than 200,000 and not more than 1,500,000, comprises a chemically and physically stable matrix which is structured by chemical cross-linking of a polymer compound such as dextran, such that it has a three-dimensional net-work structure. Gel filtration is preferably carried out, illustratively, by the use of "Sephacryl S-200HR" (maximum molecular weight fractionation of 250,000), "Sephacryl S-300HR" (maximum molecular weight fractionation of 500,000) and the like produced by Pharmacia LKB Biotechnology Co., Ltd., and "Sephacryl S-200HR" is particularly preferably employed from the view point of improving the specific activity of inhibiting colony formation of CFU-E.

The above concentrated solution is filtered by the above-mentioned gel using an eluate such as ammonium acetate, sodium phosphate and trishydrochloric acid, then the fraction corresponding to the first fraction is collected by measuring the absorbancy at 280 nm and it is de-salted and freeze-dried to obtain the hematopoietic inhibiting fraction.

The most important use of the hematopoietic inhibiting factor of the present invention is to prepare an antibody using this hematopoietic inhibiting factor as the antigen. An analytical kit can be produced by immobilizing this antibody and used for an assay to specify the cause of the anemia. The antibody can also be immobilized on a column, and used for therapeutic removal of the hematopoietic inhibiting factor as well. It can be used singly to control excess production of blood erythrocytic cells in erythrocytosis. The anemia can be improved by administration of such a drug that can control or inactivate the effect of the hematopoietic inhibiting factor.

Besides, according to the present invention, AI component can be so removed by the use of the above-mentioned dialysis membrane as to satisfy AI/AA≧1/50, wherein AI is the height of the absorbancy value of the hematopoietic inhibiting factor-containing compositions and AA is the height of the maximum absorbancy value in a gel filtration pattern of solutes of the dialysate expressed in terms of the absorbancy at 280 nm. Or, AI component can also be further removed to satisfy AI/AA≧1/30. Here, AI/AA is an average value obtained by dialyses at blood flow rate of 200 ml/min and dialysate flow rate of 500 ml/min, carried out on 20 hemodialysis patients.

According to the present invention, drug compositions, more specifically, a therapeutic agent for erythrocytosis which contains the above-mentioned hematopoietic inhibiting factor as the active ingredient can be obtained as well.

For the use as the medical and pharmaceutical compositions and a therapeutic agent for erythrocytosis, the hematopoietic inhibiting factor can be used as it is, or mixed with a known and pharmaceutically acceptable carrier or a diluting agent and the like. The administration can be either oral administration using tablets, capsules, powders, granules, pills and the like, or parenteral administration using injections, syrups, ointments, suppositories, and the like. The dose varies depending upon the administration object, the route of administration, and the conditions of a patient and the like, however, generally the dose for an adult is about 0.1 mg to 5 g, preferably about 1 mg to 2 g, and it is orally or parenterally administered in 1 to 4 portions a day, or once 1 to 7 days interval.

Embodiments

Embodiment 1

A dialysis membrane was produced according to the following process.

A spinning dope wherein 15 parts by weight of isotactic polymethyl methacrylate polymerized with Grignard reagent and 75 parts by weight of syndiotactic polymethyl methacrylate obtained by suspension polymerization were dissolved in 260 parts by weight of dimethyl sulfoxide, was delivered from outside of a ring spinning nozzle, while wet air having a dry-bulb temperature of 12° C. end m dew point of 0° C. was blown onto it to form a hollow fiber. The fiber was solidified and desolvated in water at 38° C. to produce a hollow fiber having an inner diameter of 245μ and an outer diameter of 305 7500 of such hollow fiber were bundled to produce a module having an effective area of 1.0 m². The membrane structure was that of a homogeneous membrane, end the average maximum diameter was 100 Å. The pore volume porosity (hereinafter abbreviated as VP) were 62%. And, the albumin sieving coefficient was 0.03.

A total of 20 literal of dialysate on the dialysate outlet side was collected from two patients who were undergoing therapeutic hemodialysis, at the blood flow rate of 200 ml/min and at the dialysate flow rate of 500 ml/min, using the dialysis membrane obtained according to the above-mentioned process, having albumin sieving coefficient of 0.03. The obtained 20 l of dimlysate was concentrated using a cellulose membrane having the molecular weight cut off 5,000 until the condensation ratio reached about 200 times, in other words, until the amount of the remaining solution became 100 ml. Out of 100 ml of the concentrated dialysate, 50 ml was then fractionated on a gel filtration column having a volume of 2 l, packed with "Sephacryl S-200HR", using 50 mM acetate-ammonium aqueous solution as an eluate, at the elution rate of 2 ml/min, and the absorbancy was detected at 280 nm to obtain mainly three peaks. The first fraction, being the first peak in decreasing order of molecular weight, as A, the next fraction mainly containing IgG, as B, and the fraction made of the biggest peak, mainly containing albumin, as C, were respectively freeze-dried to produce samples. The inhibition of the colony formation of CFU-E was tested for A, B and C, according to a process similar to the generally-used methyl cellulose method.

Bone marrow cells were taken out of femurs of mice (C57BL/6) then the number of the cells were controlled to be $10^7$ cells/ml after adherents were removed. Methyl cellulose of 4,000 cps was so dissolved in α-minimum essential medium alpha medium (hereinafter abbreviated as α-MEM) as to give a concentration of 1.8%. Fetal bovine serum (hereinafter abbreviated as FBS) was lot-checked beforehand. Bovine serum albumin (hereinafter abbreviated as BSA) was de-ionized and dissolved in α-MEM to give a concentration of 10%. To a 35 mm dish with 2 mm grid, 0.5 ml of 1.8% methyl cellulose solution, 0.3 ml of FBS, 0.1 ml of 10% BSA and 0.1 ml of cell suspension solution, 0.5 U of human urine erythropoietin, and 0.1 ml of the sample dissolved in α-MEM were added, and incubated at 37 in a 95% air, 5% $CO_2$ humidified atmosphere for 48 hours, then the number of CFU-E colonies per 1 cm² was counted by microscopy. The colony forming ratio was obtained by dividing the number of the colonies obtained when the sample was added by the number of the colonies obtained when only α-MEM was added instead of the sample. The colony forming ratios of A, B and C each are shown in Table 1. The low colony forming ratio of A, which corresponds to the first fraction, showed that the hematopoietic inhibiting factor-containing compositions were obtained in A.

TABLE 1

| Sample | Colony Forming Ratio (%)<br>(Mean Standard deviation (measured number)) |
|---|---|
| A | 19.6 ± 14.5 (10) |
| B | 81.2 ± 25.2 (4) |
| C | 82.5 ± 12.2 (3) |

The hematopoietic inhibiting factor-containing compositions obtained according to the above-mentioned process were assessed as follows. Firstly, the solubility of the hematopoietic inhibiting factor-containing compositions was examined as follows. The hematopoietic inhibiting factor-containing compositions were dissolved in 10 mM acetate-ammonium aqueous solution, then butanol was added to it and shaken then allowed to stand to be separated into two phases, then each of them was fractionated and freeze-dried. The assessment of the inhibition of colony formation of the CFU-E by each substance showed that the inhibitory effect remained in the aqueous solution and the substance transferred to the butanol had no inhibitory effect at all. This shows that the hematopoietic inhibiting factor is water-soluble and is not dissolved in butanol. Similarly, colony formation inhibition was assessed by the use of extraction method using chloroform-methanol- acetate-ammonium aqueous solution, and the substance which transferred to chloroform showed no inhibitory effect at all. The transferring to n-hexane was also tested but no inhibitory effect was found at all. From these results, it is found out that the hematopoietic inhibiting factor is a water-soluble substance having such a feature that is not dissolved in a material such as butanol, chloroform and n-hexane.

Then, heat stability of the hematopoietic inhibiting factor was examined as follows. The hematopoietic inhibiting factor was dissolved in 10 mM acetate-ammonium aqueous solution at a concentration of 1 mg/ml, then treated at 100° C. for 10 minutes, 20 minutes and 30 minutes and freeze-dried. Assessment of the inhibition of colony formation of CFU-E by each of them showed that the product treated at 100° C. for 10 minutes had inhibitory effect, the product treated for 20 minutes had half-reduced inhibitory effect, and the product treated at 100° C. for 30 minutes had no inhibitory effect at all. Accordingly, the hematopoietic inhibiting factor was found to be a substance resistant to heat-treatment at 100° C. for 10 minutes.

The amino acid sequence from N-terminal of the hematopoietic inhibiting factor was examined as follows. After the hematopoietic inhibiting factor-containing compositions were dissolved in buffer containing sodium dodecyl sulfate (hereinafter abbreviated as SDS), it was heated at 100° C. for 2 minutes, then analyzed by normal SDS polyacryl amide gel electrophoresis (hereinafter abbreviated as PAGE) method. Then the protein was blotted transcribed onto a hydrophobic membrane. (polyvinyliden fluoride membrane) from the electrophoresis gel nsing a transcription apparatus. The protein blotted on the membrane was stained with Coomassie brilliant blue as bands, and each band was analyzed by amino acid sequence automatic analyzer (protein sequencer) of Edman method. The amino acid sequence wherein the sequence of amino acids from the N-terminal of the hematopoietic inhibiting factor to the 19th is expressed as Ala-Val-Val-Tyr-Asp-Lys-Asp-Gly-Thr-Ser-Phe-Asp-Ile-Tyr-Gly-Lys-Val-Gln-Ala (SEQ ID NO:1) was obtained from the band which was migrated by SPS-PAGE to the position of the molecular weight of around 40,000. The amino acid sequence wherein the sequence of amino acids from the N-terminal of the hematopoietic inhibiting factor to the 10th is expressed as Ala-Ala-Lys-Slu-Val-Lys-Phe-Gly-Asn-Glu (SEQ ID NO:2) was obtained from a band which was migrated by SDS-PAGE to the position of the molecular weight of around 70,000.

Embodiment 2

The dialysis was carried out in a way analogous to that of Embodiment 1, and 100 ml of the dialysate was respectively collected from three patients on the dialysis outlet side 4 hours after starting the dialysis, then concentrated 100-fold, and each of them was filtered by gel filtration with 'HiLoad Sephacryl S-200HR 16/60 then the absorbancy was measured at 280 nm. The values AI/AA for three patients were respectively 1/14, 1/47 and 1/21. The gel filtration pattern for the case of 1/14 is shown in FIG. 1.

Embodiment 3

The albumin sieving coefficient of a membrane obtained in a process described in Embodiment 1, but changing the temperature for solidification and desolvation during the dialysis membrane formation process, from 38° C. to 25° C. was 0.01.

The obtained dialysis membrane was used for the process analogous to that of Embodiment 2, to obtain the absorbancy values of A, B, C at 280 nm, which were not more than half of those obtained in Embodiment 1. The AI/AA obtained this time in a process analogous to that of Embodiment 2 was 1/40.

Industrial Applicability

Hematopoietic inhibiting factor-containing compositions which inhibit colony formation of CFU-E can be obtained.

Moreover, a process of treating blood in which AI component can be so removed as to satisfy AI/AA≧1/50, wherein AI is the height of the absorbancy value of the hematopoietic inhibiting factor-containing compositions and AA is the height of the maximum absorbancy value in a gel filtration pattern of solutes of the dialysate expressed in terms of the absorbancy at 280 nm, and a dialysis membrane which satisfies AI/AA≧1/50, wherein AI is the height of the absorbancy value of the hematopoietic inhibiting factor-containing compositions and AA is the height of the maximum absorbancy value in a gel filtration pattern of solutes of the dialysate expressed in terms of the absorbancy at 280 nm can be provided. Besides, it is also possible to provide drug compositions and a therapeutic agent for erythrocytosis, containing such hematopoietic inhibiting factor as the active ingredient.

We claim:

1. A dialysis membrane which satisfies AI/AA≧1/50, wherein

AI is the height of the absorbency value of a hematopoietic inhibiting factor-containing composition obtained by separating a component having a molecular weight of 200,000 or more from a dialysate obtained by dialyzing blood with a dialysis membrane of albumin sieving coefficient of not less than 0.01, and AA is the height of the maximum absorbency value in a gel filtration pattern of solutes of the dialysate expressed in terms of the absorbency at 280 nm.

2. A dialysis membrane which satisfies the relationship AI/AA≧1/50, wherein

AI is the height of the absorbency value of a hematopoietic inhibiting factor-containing composition which can be obtained on a macromolecular side by separating a dialysate obtained by dialyzing blood with a dialysis membrane of albumin sieving coefficient of not less than 0.01, using a gel having a maximum molecular weight fraction of not less than 200,000, and AA is the height of the maximum absorbency value in a gel filtration pattern of solutes of the dialysate expressed in terms of the absorbency at 280 nm.

3. A dialysis membrane which satisfies the relationship AI/AA≧1/50, wherein

AI is the height of the absorbency value of a hematopoietic inhibiting factor-containing composition which inhibits colony formation of an erythroid colony forming cell and which can be obtained in the fraction eluting at an exclusion limit by gel filtration using a gel having maximum molecular weight fraction of not less than 200,000 and not more than 1,500,000 of a dialysate of blood which is obtained with a dialysis membrane having an albumin sieving coefficient of not less than 0.01, followed by concentration with a membrane having molecular weight fraction of not more than 5,000 and AA is the height of the maximum absorbency value in a gel filtration pattern of solutes of the dialysate expressed in terms of the absorbency at 280 nm.

4. A dialysis membrane which satisfies the relationship AI/AA≧1/50 according to claim 1, wherein the albumin sieving coefficient of the dialysis membrane is not less than 0.02.

5. A dialysis membrane which satisfies the relationship AI/AA≧1/50 according to claim 1, wherein the albumin sieving coefficient of the dialysis membrane is not less than 0.03.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 19 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:1:

Ala Val Val Tyr Asp Lys Asp Gly Thr Ser Phe Asp Ile Tyr Gly Lys
 1           5                   10                  15
Val Gln Ala ( 2 ) INFORMATION FOR SEQ ID NO:2:

( i ) SEQUENCE CHARACTERISTICS:
    ( A ) LENGTH: 10 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:2:

Ala Ala Lys Glu Val Lys Phe Gly Asn Glu
 1           5                   10